United States Patent [19]
Stalker et al.

[11] Patent Number: 5,908,395
[45] Date of Patent: Jun. 1, 1999

[54] VIBRATING GUIDEWIRE

[75] Inventors: Kent C. B. Stalker, San Diego; Edward J. Nance, Corona, both of Calif.

[73] Assignee: Advanced Cardiovascular Systems, Inc., Santa Clara, Calif.

[21] Appl. No.: 08/822,150

[22] Filed: Mar. 17, 1997

[51] Int. Cl.[6] .................................................. A61B 5/103
[52] U.S. Cl. ............................................................ 600/585
[58] Field of Search .................................... 600/434, 435, 600/585; 606/159

[56]         References Cited
       U.S. PATENT DOCUMENTS

| | | | |
|---|---|---|---|
| 4,854,325 | 8/1989 | Stevens | 128/657 |
| 5,120,323 | 6/1992 | Shockey et al. | 604/282 |
| 5,243,997 | 9/1993 | Uflacker et al. | 128/772 |
| 5,443,078 | 8/1995 | Uflacker | 128/772 |
| 5,524,635 | 6/1996 | Uflacker et al. | 128/772 |
| 5,549,119 | 8/1996 | Solar | 600/585 |
| 5,776,153 | 7/1998 | Rees | 606/159 |

FOREIGN PATENT DOCUMENTS

WO 95/01752   1/1995   WIPO.

*Primary Examiner*—Max Hindenburg
*Attorney, Agent, or Firm*—Heller, Ehrman, White & McAuliffe

[57] ABSTRACT

The invention is directed to a hand held vibration device which imparts reciprocating motion in a guidewire while leaving the guidewire free to rotate about its longitudinal axis, to facilitate advancement of the guidewire through a highly occluded blood vessel. The vibrating device is provided with a lock ring for reversibly preventing guidewire rotation without effecting guidewire reciprocation, and the reciprocation length of the device may be varied. The length the guidewire extends past the distal end of a delivery catheter may be varied from controls on the device which do not require guidewire detachment from the reciprocating mechanism. The device may be used with or without a delivery catheter provided with a curved distal end, the curvature of which can be varied while the catheter is inside the patient.

9 Claims, 9 Drawing Sheets

VIBRATING GUIDEWIRE

BACKGROUND OF THE INVENTION

This invention relates to the field of medical devices, and more particularly to a guidewire system for advancement through a highly occluded blood vessel.

Atherosclerosis resulting in a blockage of arteries can be a life threatening disease. Percutaneous intravascular procedures such as angioplasty and atherectomy were developed to open blocked vessels with as little trauma as possible. Angioplasty involves inflating a balloon positioned within the obstructive deposits or stenosis in the vessel, so that the stenosis is compressed against the arterial wall and the wall expanded to open up the passageway. Atherectomy involves selective excision and removal of obstructive deposits from the vessel walls.

An essential first step in these percutaneous procedures is maneuvering the distal operative extremity of the angioplasty or atherectomy catheter into position at a precise point inside the arterial occlusion. Maneuvering through small branched vessels and the stenosis itself can be very difficult and tedious. Especially difficult in this respect are chronic total occlusions (CTO). While most CTOs are not totally obstructed, only a small tortuous channel passes through the stenosis.

The guidance system used to position the catheters must be both effective and safe, because if they cannot be positioned precisely into place, the stenosis cannot be treated. Additionally, inadequate guidance carries a risk of perforation of the vessel that exceeds the benefits of recanalization.

The use of a guidewire is ideal in terms of effectiveness, safety, simplicity, and cost. Typically, a guiding catheter is inserted into the patient's aorta with its distal tip seated in the ostium of the desired coronary artery. The guidewire is then maneuvered into place while its progress is fluoroscopically monitored. Once the guidewire passes through the stenosis, the angioplasty or atherectomy catheters can be advanced over the guidewire and into place within the stenosis.

The distal end of the guidewire may be shaped, e.g. bent, at an angle up to 90° from its longitudinal axis, so that torquing the proximal end of the guidewire from outside the patient can guide the distal tip of the guidewire into branch arteries. While it is known that vibrating a guidewire can help its passage through an occluded artery, such vibration has not been shown to be successful in highly occluded passageways such as CTO's.

What has been needed is a vibration device with the superior guidewire steerability and ease of use which results from having the guidewire free to rotate or move longitudinally relative to the distal tip of a guiding catheter even though the guidewire is attached to the vibrating mechanism. By providing for simultaneous manipulation of more than one variable of the guidewire, such a device gives the operator greater control over the guidewire position. Furthermore, such a device would have superior ease of use because unclasping, repositioning, and reclasping the guidewire to the vibration mechanism would not be required each time the guidewire needed to be rotated or moved relative to the guiding catheter.

Additional guidewire control would be provided by a guiding catheter with a bend in the distal tip which could be varied incrementally from 0° to 90° from its axis, while the catheter was inside a patient vessel. When attached to a vibrating device, a catheter with such in situ variability would allow the distal end of the guidewire to oscillate at a variety of angles to the longitudinal axis of the catheter, and would be useful in accessing off-center channels and side branches.

The vibration device of the present invention provides such a combination of desirable properties.

SUMMARY OF THE INVENTION

The present invention is directed to a guidewire vibration device for use with or without a guidewire guiding catheter, to aid in advancement of a guidewire through a patient vessel. The vibration device of the invention generally has a guidewire tube reciprocally driven by a motor, designed to provide superior steerability in a reciprocating guidewire.

The vibration device has a housing, an electric motor within the housing, and a cam attached to the motor which translates the motor's rotational output into repetitive linear motion. A reciprocating member attaches to the cam to vibrate with a pivoting action. A tube is attached to the reciprocating member so that the tube reciprocates with the reciprocating member along the tube's longitudinal axis but remains free to rotate around the longitudinal axis. A suitable connection is a ball and socket joint formed by a ball on the tube which fits into a socket on the reciprocating member. A guidewire threads through the lumen of the tube, and is releasably attached to the proximal end of the tube.

The rotation of the guidewire tube may be unchecked, or a locking mechanism may be used. A suitable locking mechanism reversibly locks the rotational motion of the tube by adjusting the circumference of an opening through which the guidewire tube extends. When narrowed, the opening is large enough to allow the tube to clear when reciprocating longitudinally but too small to allow corners of the tube to clear if tube rotation is attempted.

In accordance with a further development of the invention a fitting attaches a guiding catheter to the vibration device. The fitting allows the guiding catheter to be reversibly extended or retracted while in use, thereby varying the length that the guidewire extends beyond the distal tip of the catheter without requiring detachment of the guidewire from the vibration device. A suitable fitting has a rotating luer ring threaded onto a distal side of the device, and a tubular support member with a proximal end attached to the rotating luer ring and a distal end attached to a luer fitting which releasably connects a guiding catheter to the tubular member. Rotation of the luer ring imparts longitudinal movement in the catheter but not in the guidewire.

In accordance with a further development of the invention, the vibration device has a variable stroke mechanism that varies the fulcrum of the reciprocating member to vary the reciprocation length. A suitable mechanism has a rotating cap threaded onto the vibration device, and a pivot block attached to the reciprocating member and the underside of the rotating cap. When the cap is rotated, the pivot block is displaced and the fulcrum of the reciprocating member is shifted, thereby varying the angle at which the reciprocating member pivots.

In a preferred embodiment, the vibration device may be used in combination with a guidewire guiding catheter that has support characteristics which can be varied while inside the patient's vessel. The guiding catheter has an outer tubular member and a inner tubular member slidably disposed within the lumen of the outer tubular member. The distal extremity of the inner tubular member is provided with a curved end which can be reversibly straightened by retracting the inner tubular member distal tip into the distal end of the outer tubular member. The inner tubular member is formed of a plastic material having a modulus of elasticity such that the curve at the distal tip straightens under applied force and subsequently returns when the force is removed. The proximal end of the inner tubular member is attached to the vibration device in a position to receive the guidewire.

The vibration device of the invention provides for ease of use and superior control in advancing a guidewire through a patient vessel. This is due to the ability to rotate the guidewire and vary the length that the guidewire extends beyond the distal tip of the guiding catheter, while the guidewire is still attached to the vibrational mechanism. With prior devices the guidewire could not be manipulated independently of the vibration device, so the operator would have to loosen the clamping mechanism that holds the guidewire to the vibration mechanism, reposition the guidewire, and then reclamp the guidewire to the vibration mechanism. Additionally, the guidewire position inside the vessel could not be manipulated very well with the prior devices because the guidewire would not be vibrated simultaneously with the other manipulations such as rotation. Furthermore, the tediousness of repeatedly releasing, repositioning, and reattaching the guidewire to the vibration mechanism adds to operator fatigue and possibly operator error or engagement with an unsterile area thereby requiring the operator to start over from the beginning with a new sterile guidewire.

The guidewire steering is further optimized by the use of the guiding catheter with a distal tip angle of curvature which can be varied while inside the patient vessel. By enabling the distal end of the guidewire to oscillate at a variety of angles to the longitudinal axis of the catheter, this in situ variability allows off-center channels and side branches to be accessed which otherwise would have been difficult or impossible to enter. These and other advantages of the invention will become more apparent from the following detailed description of the invention and the accompanying exemplary drawings.

DETAILED DESCRIPTION OF THE INVENTION

Figure 1:
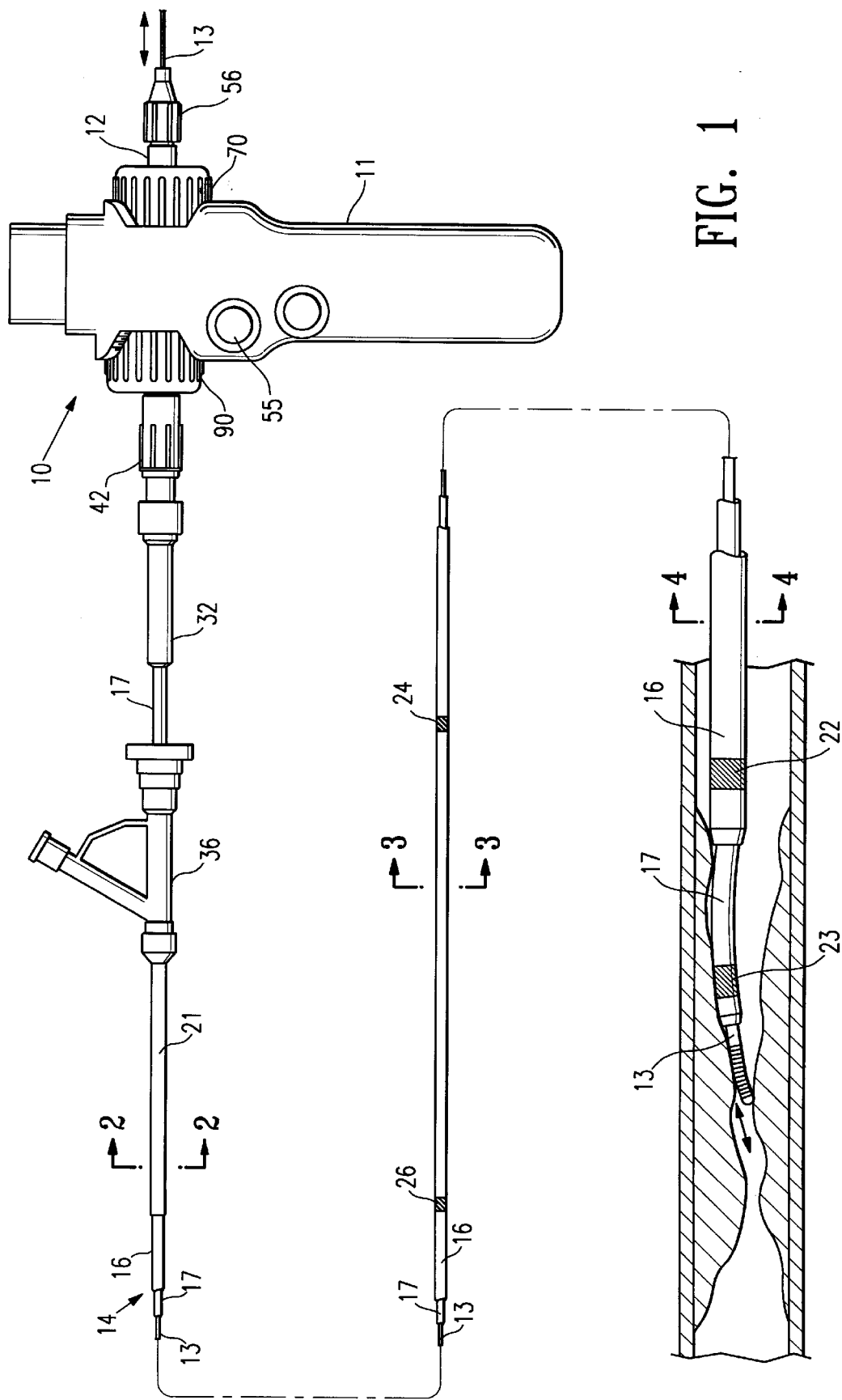
FIG. 1 is an elevational schematic view of a guidewire vibration device embodying features of the invention.

A guidewire vibration device 10 embodying features of the invention is illustrated in FIG. 1, and generally includes a housing 11 connected to a guidewire tube 12 having a lumen configured to slidably receive a guidewire 13 suitable for advancement through a patient's coronary and peripheral blood vessels.

Figure 3:
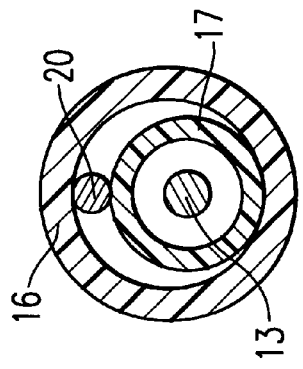
FIG. 3 is a transverse cross-sectional view of the guidewire delivery catheter shown in FIG. 1 taken along lines 3—3.
Figure 4:
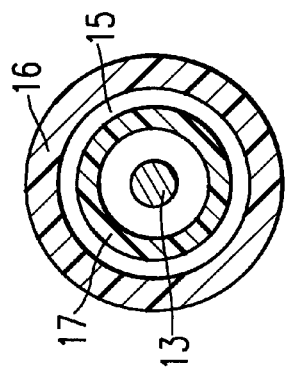
FIG. 4 is a transverse cross-sectional view of the guidewire delivery catheter shown in FIG. 1 taken along lines 4—4.
Figure 2:
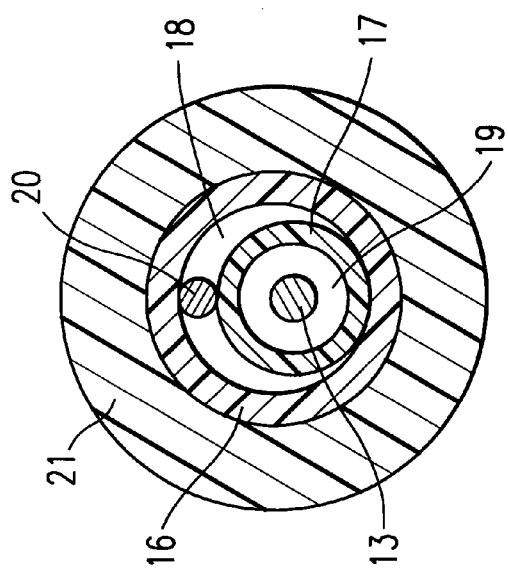
FIG. 2 is a transverse cross-sectional view of the guidewire delivery catheter shown in FIG. 1 taken along lines 2—2.

Referring to FIG. 1, a presently preferred embodiment of the invention includes a delivery catheter 14 which may be attached to the vibration device 10 to facilitate directing the catheter operative end to a desired location. FIGS. 2–4 illustrate transverse cross-sections of the delivery catheter 14 taken along FIG. 1 lines 2—2, 3—3, and 4—4 respectively. The delivery catheter 14 has an outer tubular member 16 and an inner tubular member 17 disposed within the outer tubular member lumen 18. The inner tubular member 17 has a lumen 19 extending therein which is configured to slidably receive the guidewire 13. A stiffening rod 20 may be provided within the outer tubular member lumen 18 to add rigidity to the outer tubular member 16. Strain relief tubing 21 may also be provided for added support at the proximal end of the outer tubular member 16. An annular space 15 is defined by the part of the outer tubular member lumen 18 existing between the inner 17 and outer 16 tubular members, and may provide a channel for introducing a liquid out the distal end of the catheter.

As can be seen in FIG. 1, the outer tubular member 16 may have a radiopaque metal tip marker 22 on its distal end for fluoroscopic observation of the tubular member, and may have printed brachial 24 and femoral 26 markings. The inner tubular member 17 may also have a radiopaque metal tip marker 23 on its distal end. More than one durometer may be spliced together so as to form a variable stiffness catheter (not shown).

Figure 5:
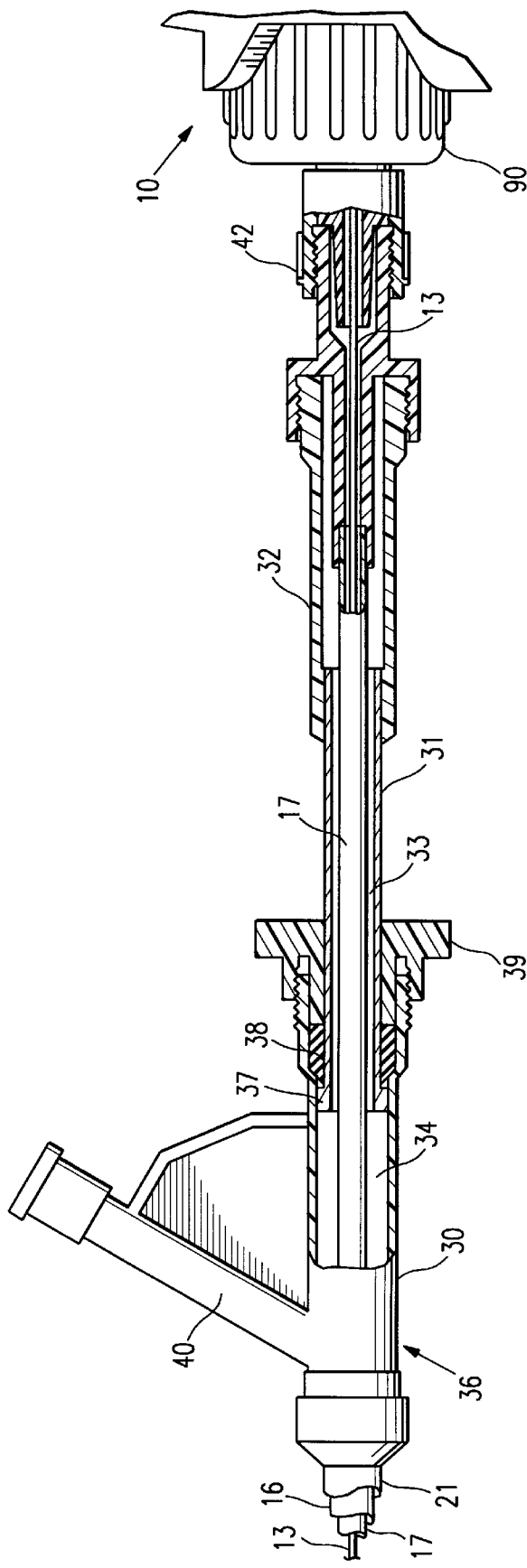
FIG. 5 is an enlarged longitudinal cross-sectional view of the proximal end of the guidewire delivery catheter shown in FIG. 1.

In the presently preferred embodiment shown in FIG. 5 the inner tubular member 17 is longer than the outer tubular member 16 and extends through a cylindrical member 30, a hollow support member 31, and terminates at its proximal end in a centerport adapter stem 32. Hollow support member 31 can be fixed to centerport adapter stem 32 by any convenient means, e.g., by cementing the two together. The inner tubular member 17 lies inside the hollow support member lumen 33 of the hollow support member 31 which is slidably received in the cylindrical member lumen 34. The cylindrical member 30 functions in part as a carriage in which the hollow support member 31 and inner tubular member 17 disposed therein are free to move along an axis parallel to the guidewire's 13 longitudinal axis. The cylindrical member 30 and outer tubular member 16 remain stationary as the inner tubular member, hollow support member 31, and vibration device 10 move longitudinally. In the embodiment shown in FIG. 5, the cylindrical member 30 is a Y-connector having a hollow side arm 40 for introducing a liquid to the annular space 15 of the outer tubular member lumen 18. Any suitable connector 36 may be used to connect the cylindrical member 30 distal end to the outer tubular member proximal end directly, or including strain relief tubing 21 connected to the outer tubular member 16. This allows the inner tubular member 17 to be moved independently of the outer tubular member 16 so that the inner tubular member distal end can be extended and retracted beyond the outer tubular member distal end.

The distal end of the hollow support member 31 may have an enlargement 37 which is larger than the port 38 at the proximal end of the cylindrical member 30 which acts as a stop to prevent the hollow support member 31 from fully disengaging from the cylindrical member 30. While a Touhy-Borst connector 39 is shown in FIG. 5 connecting the hollow support member 31 to the cylindrical member 30, any suitable connector may be used. FIG. 5 shows a luer connector 42 securing the proximal extremity of the delivery catheter 17 to the vibration device 10, although any suitable connector may be used.

Figure 6:
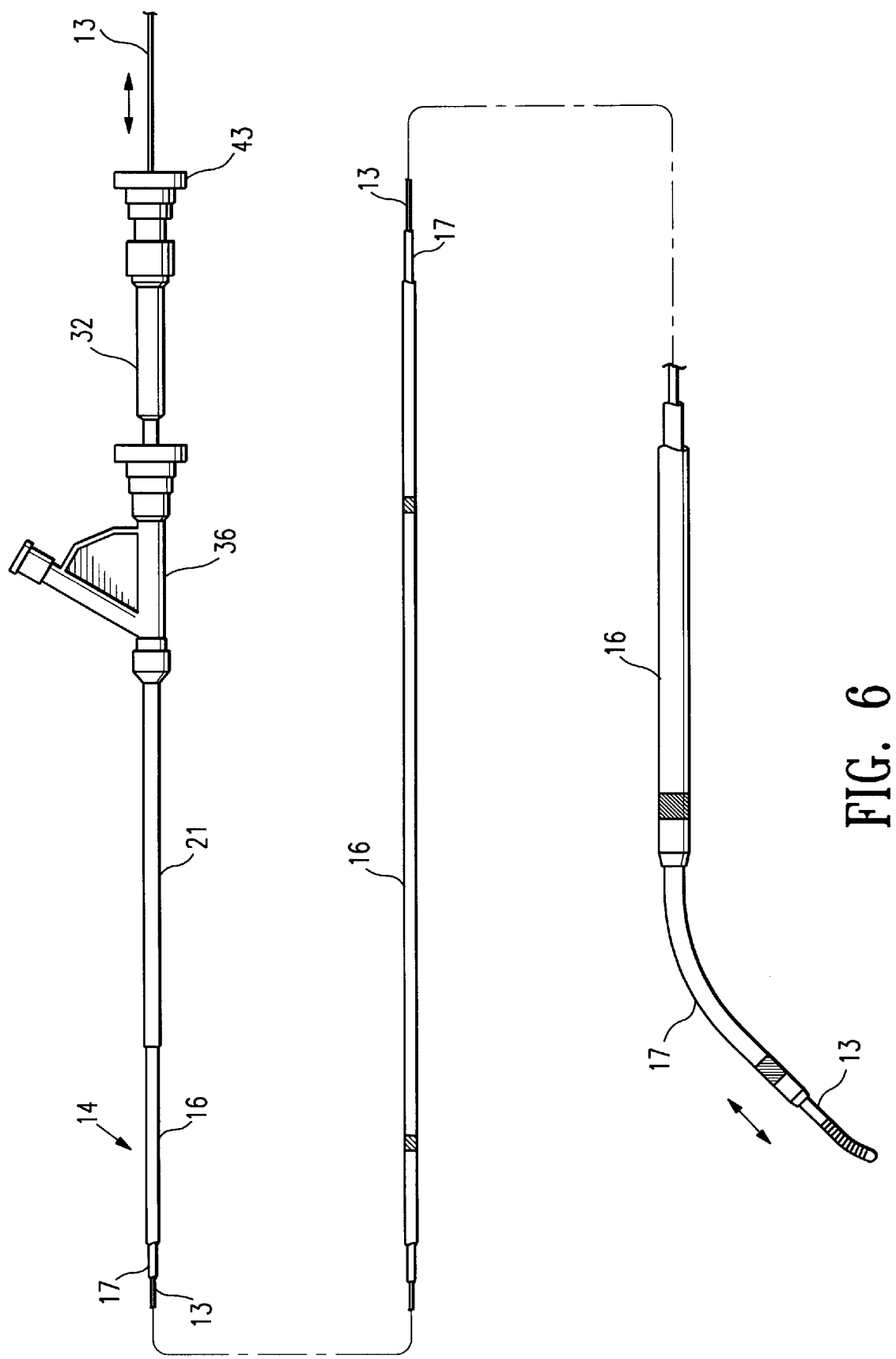
FIG. 6 is an elevational schematic view of a guidewire delivery catheter configured for manual vibration, illustrating the inner tubular member extending out the outer tubular member.

FIG. 6 illustrates the delivery catheter 14 configured for use in manual guidewire vibration, in which case a Touhy-Borst connector 43 is provided in place of the aforementioned luer connector 42 at the proximal extremity of the delivery catheter 14.

Figure 7:
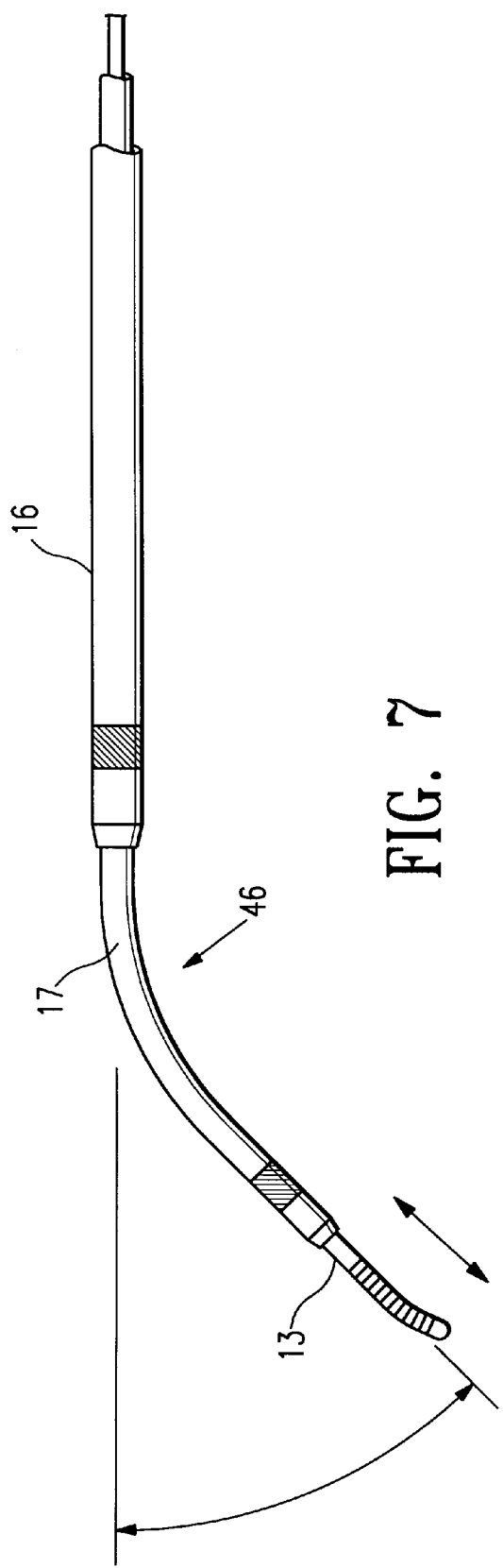
FIG. 7 is an enlarged view of the distal end of the guidewire delivery catheter shown in FIG. 1 illustrating the inner tubular member extending out the outer tubular member.
Figure 8:
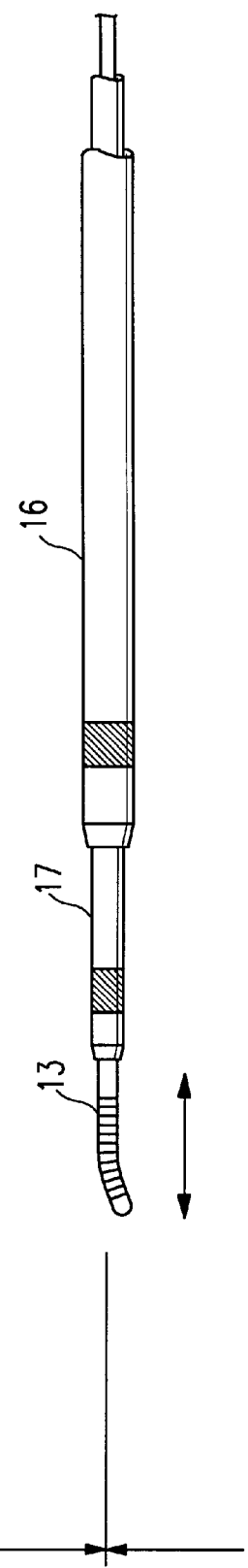
FIG. 8 is an enlarged view of the distal end of the guidewire delivery catheter shown in FIG. 1 illustrating the inner tubular member withdrawn into the outer tubular member.

The distal end of the inner tubular member 17 has a preformed curve 46 bent at an angle up to 90° from its axis, and the inner tubular member is formed of a flexible plastic material having a modulus of elasticity such that the curve 46 at the distal end straightens under applied force and subsequently returns to its original shape when the force is removed. As shown in FIG. 7, when the inner tubular member 17 is fully extended out the distal end of the outer tubular member 16, its distal end is curved. FIG. 8 shows that withdrawing the inner tubular member 17 into the outer tubular member 16 straightens the curve at the distal end of the catheter.

The extent to which the inner tubular member 17 is extended beyond the distal end of the outer tubular member 16 controls the degree to which the distal end is bent. In a presently preferred embodiment, the inner tubular member 17 is of a length such that it can extend a maximum of about 3 centimeters past the distal end of the outer tubular member 16. When the inner tubular member 17 is extended or retracted relative to the outer tubular member distal end, the guidewire 13 position relative to the inner tubular member 17 does not change when the guidewire is secured to the vibration device 10.

Figure 9:
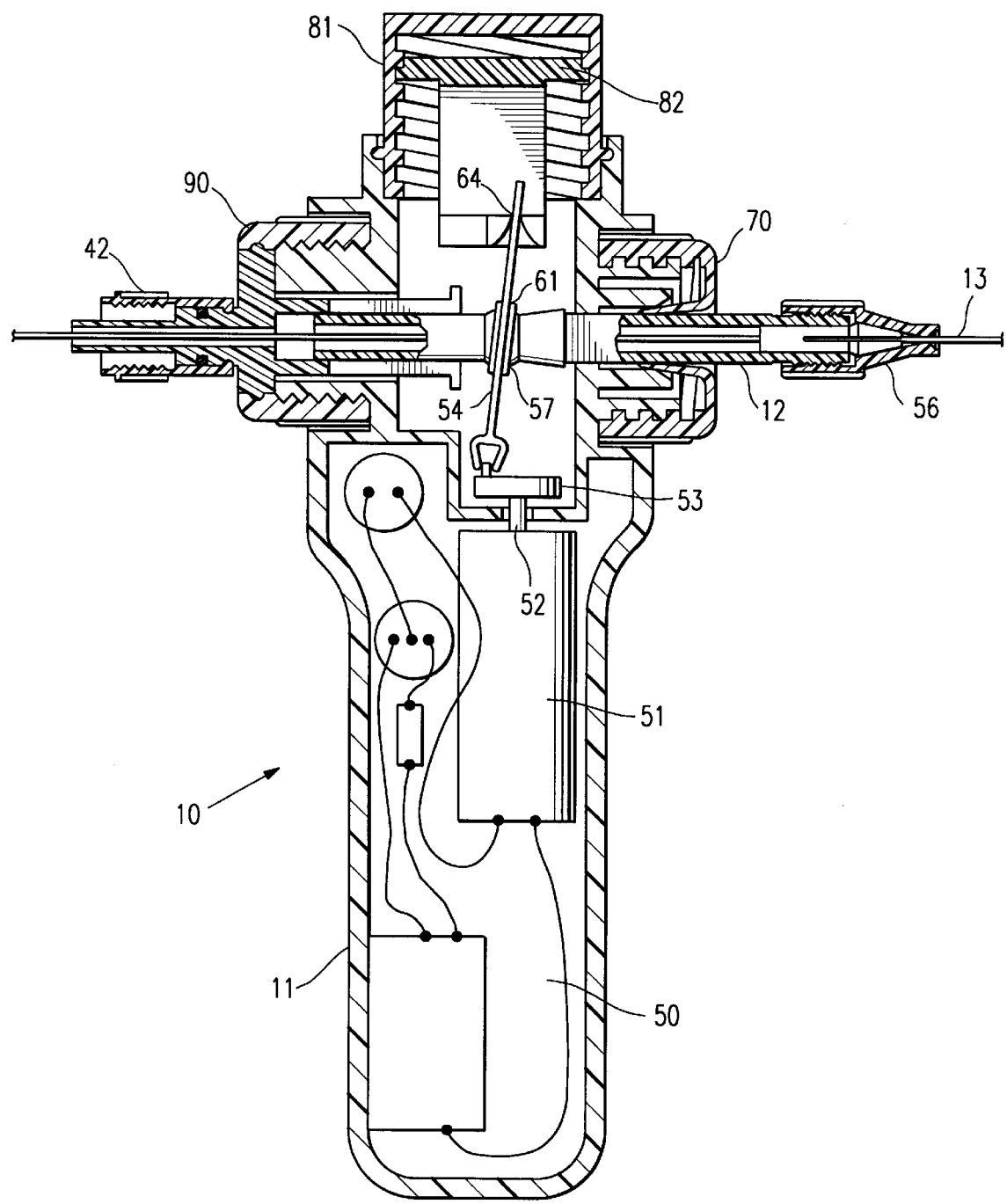
FIG. 9 is a cross-sectional view of the guidewire vibration device shown in FIG. 1.
Figure 10:
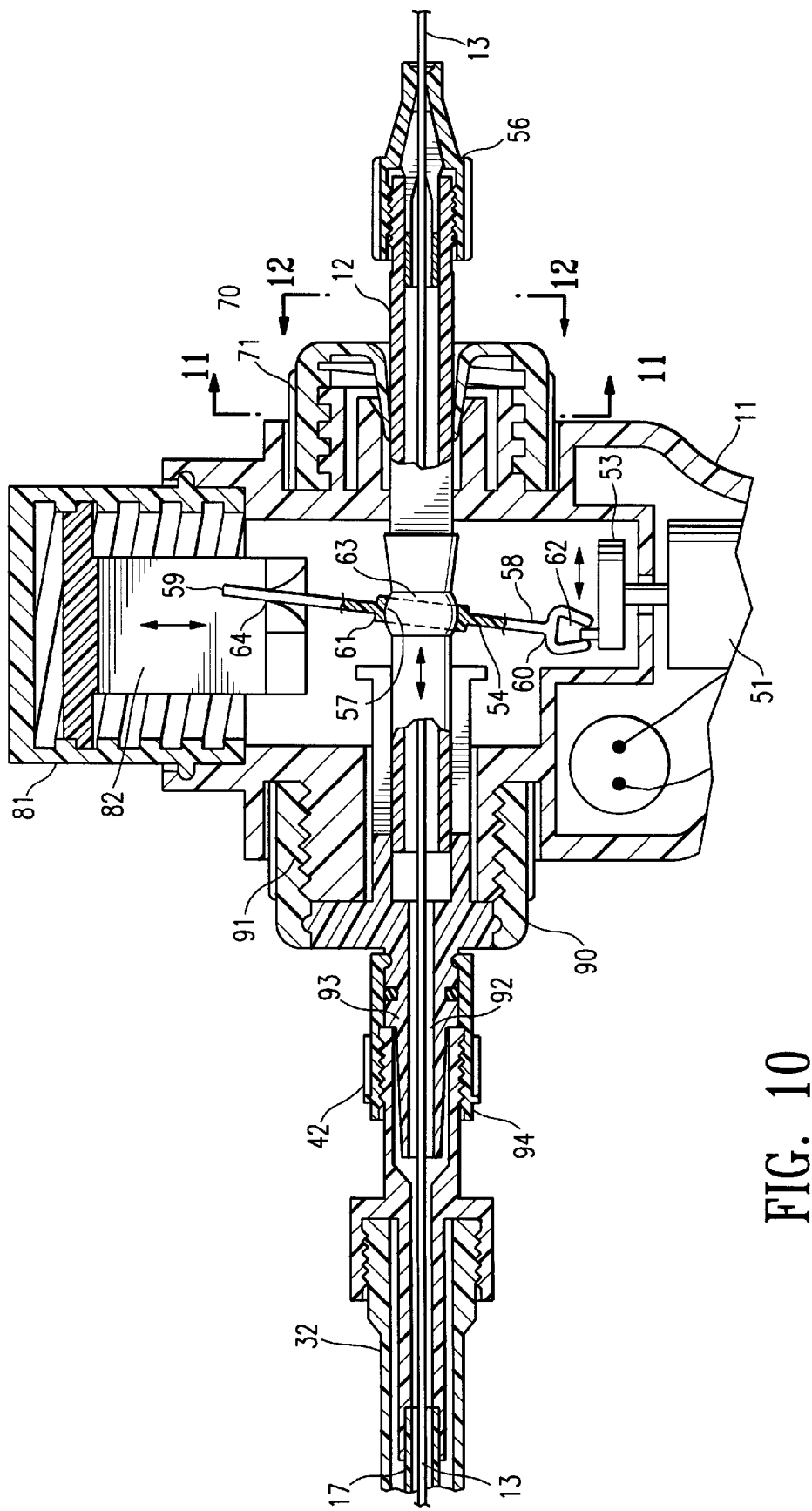
FIG. 10 is a fragmentary cross-sectional view of the device of FIG. 1 illustrating a reciprocating lever and a pivot block.
Figure 11:
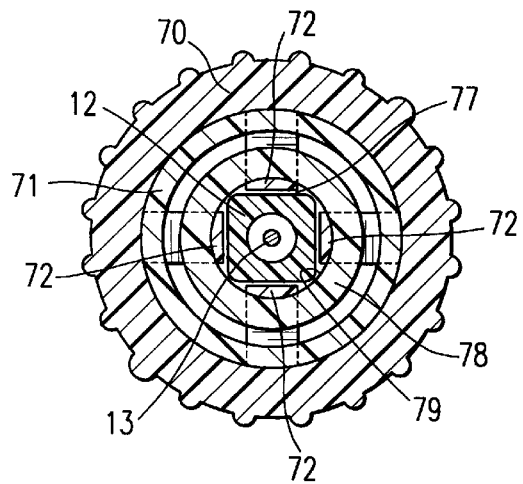
FIGS. 11 and 12 are transverse cross-sectional views of the rotating lock ring shown in FIG. 10.

The delivery catheter 14 may be formed of materials common in delivery catheter design. The inner 17 and outer 16 tubular members may be made of any number of polymeric materials, and the inner and outer tubular members preferably possess a low coefficient of friction with respect to one another to facilitate the advancement of the inner tubular member 17 and that of the guidewire 13 as well. An alternative embodiment (not shown) including an outer tubular member made up of a plurality of tube lengths of different diameter, where each proximal tube has a diameter larger than the tube distal thereto so that they may be inserted one into the other, may be used to provide a delivery catheter with variable rigidity The internal components of the vibration device 10 shown in FIG. 1 are best illustrated in FIGS. 9 and 10. Referring now to FIG. 9, the housing 11 has an interior chamber 50 containing a motor 51 with a rotary output shaft 52. The motor output shaft 52 turns a cam 53 which travels in an orbital motion. The cam 53 imparts reciprocating motion to a reciprocating member 54, the guidewire tube 12, a collet 56, and a guidewire 13 positioned within the guidewire tube 12 and collet 56. The reciprocating member 54 generally has a bore 57 to connect with the guidewire tube 12. The arrangement described protects the guidewire from direct exposure to the electrical components of the system. This guards against current leakage onto the guidewire.

A specific embodiment of the invention is illustrated in FIGS. 9 and 10. Referring now to FIG. 10, the reciprocating member 54 is a reciprocating lever 58 which reciprocates the guidewire tube 12. The reciprocating lever 58 has a first end 59, a second end 60, a socket 61, and a groove 62 in the second end which operatively engages with the cam 53 to translate the cam orbital motion to reciprocating motion. The reciprocating lever 58 reciprocates about its fulcrum 64. The socket 61 extends through the reciprocating lever 58 and is sized to mate with an expanded section 63 on the guidewire tube 12. This allows the guidewire tube 12 to reciprocate with the reciprocating lever 58 while remaining free to rotate around the guidewire tube longitudinal axis. The socket 61 is shown in dashed lines in FIG. 10 to better illustrate the expanded section 63 on the guidewire tube 12.

Figure 12:
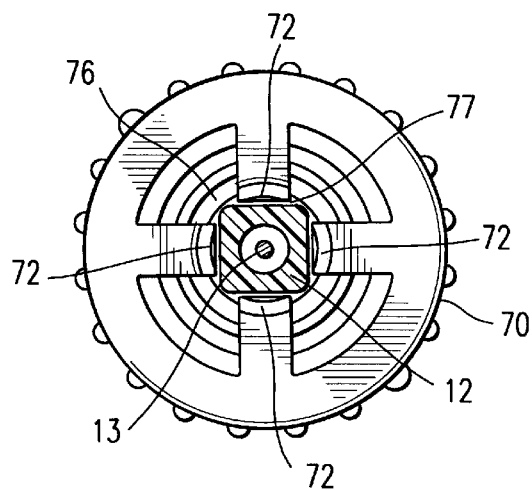
Figure 13:
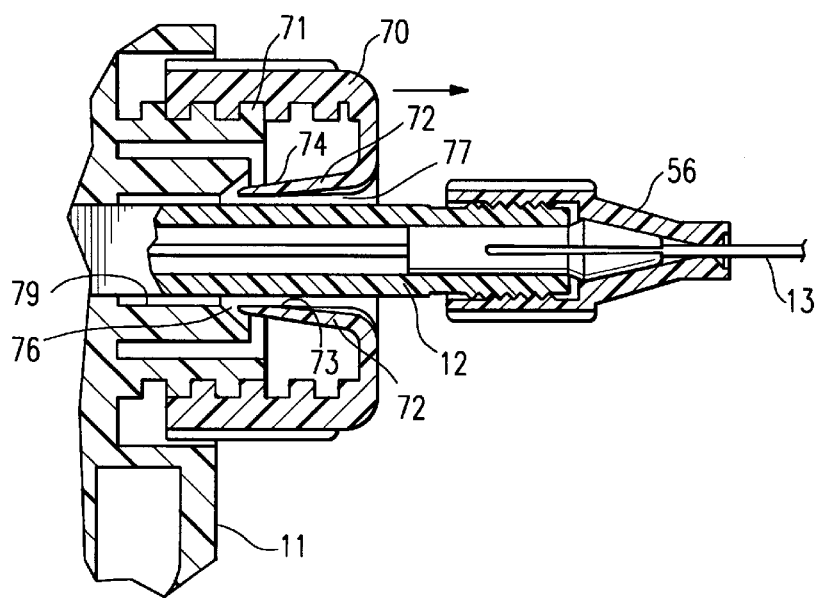
FIG. 13 is a fragmentary cross-sectional view of the rotating lock ring shown in FIG. 10 in the unlocked position.

Illustrated in FIGS. 10–13 is a rotating lock ring 70 which attaches to a first externally threaded cylindrical extension 71 on the housing 11 and which can be rotated to prevent the guidewire tube 12 from rotating about its longitudinal axis. The rotating lock ring 70 is best shown in FIG. 13 and has a plurality of arms 72, having outer sides 73 and inner sides 74, which extend diagonally down into the core 76 of the lock ring 70 to form an opening 77 through which the guidewire tube 12 extends. A boss 78 having an inner face 79 is provided on the housing 11, and when the lock ring 70 is rotated and moved into the locked position the inner face 79 of the boss 78 contacts the outer sides 73 of the arms 72, forcing the arms inward and narrowing the opening 77 formed by the arms 72. FIG. 10 shows the rotating lock ring 70 in a locked position in which the guidewire tube 12 will contact the arms 72 if rotation is attempted but remains free to reciprocate longitudinally through the opening 77. FIG. 13 shows the rotating lock ring 70 in the unlocked position in which the arms 72 are not in contact with the boss 78. The material used for the arms 72 should be such that bending of the arms 72 when in the locked position does not exceed the elastic limit of the material so that they will not permanently deform when in the locked position.

FIG. 12 shows a cross-sectional view of the rotating lock ring 72 along lines 12—12 in FIG. 10, and illustrates a most preferred embodiment having four arms forming a square opening through which a guidewire tube 12 having four flat sides extends. Other lock ring configurations which reversibly alter the opening through which the guidewire tube 12 extends may be suitable. For example a lock ring with an axis offset from the guidewire tube's axis and with an opening that is circular with two flat sides meeting to form an angle of about 90°, will allow guidewire tube rotation when the guidewire tube is close to the circular region of the opening but prevent it when rotation of the lock ring moves the flat sides closer to the guidewire tube (not shown).

Referring again to FIG. 10, a rotating cap 81 may be provided which is threaded onto the housing 11 of the vibration device which may be used to change the stroke length of the reciprocating lever 58. The rotating cap 81 is attached to a pivot block 82 and cap rotation imparts linear motion to the pivot block. The pivot block is attached to the reciprocating lever 58 at a point of contact which varies as the rotating cap 81 is rotated and the pivot block 82 is linearly displaced. This point of contact is the fulcrum 64 on which the reciprocating lever 58 reciprocates so the rotating cap 81 and pivot block 82 together change the stroke length of the reciprocating lever 58 by changing the lever's fulcrum 64.

Figure 14:
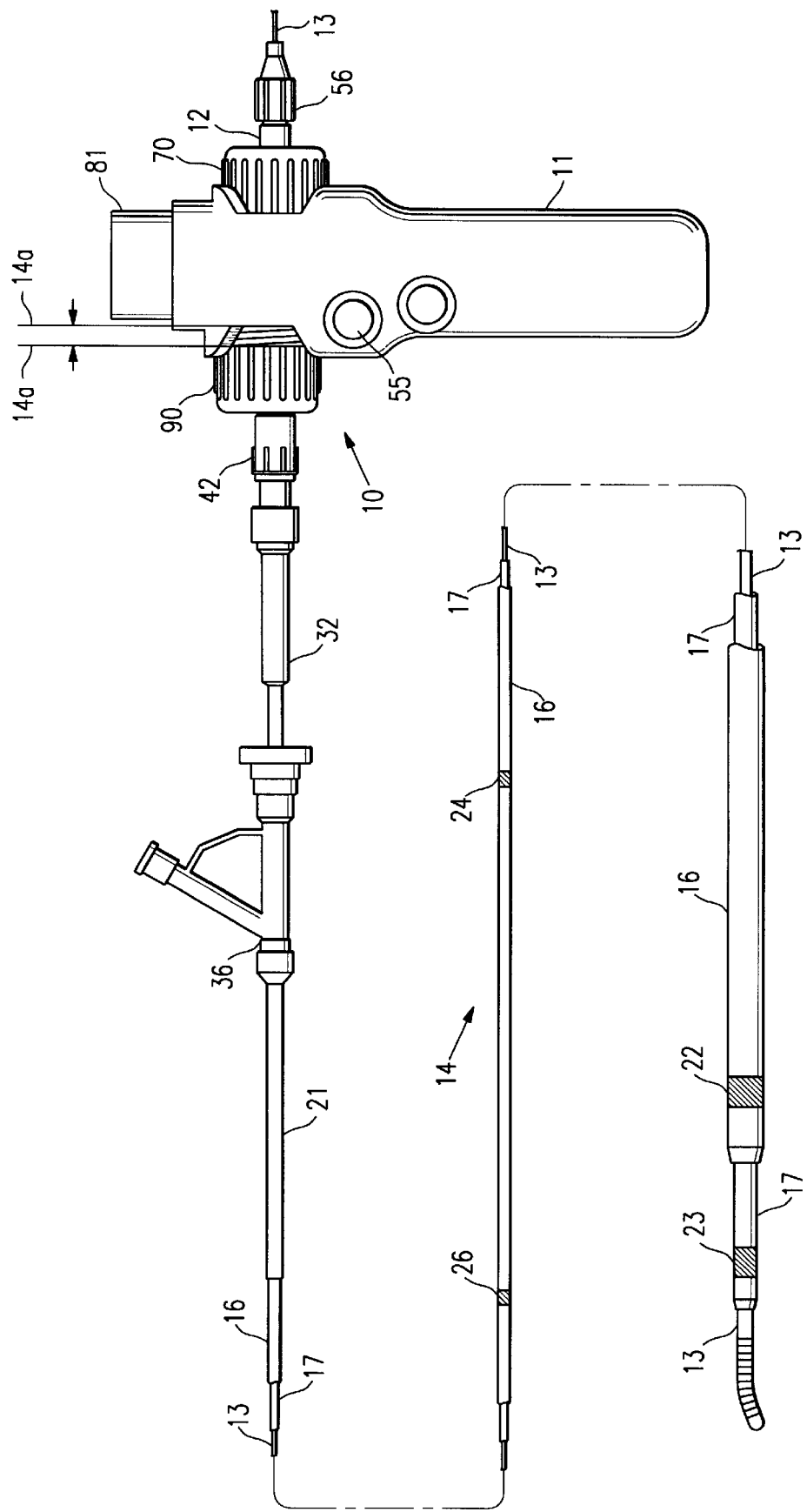
FIG. 14 is an elevational schematic view of the device shown in FIG. 1 illustrating the action of the rotating luer ring imparting motion to the delivery sheath.

FIG. 10 best illustrates a rotating luer ring 90 which attaches to a second externally threaded cylindrical extension 91 on the housing 11 and which can be rotated to impart longitudinal motion in the guidewire delivery catheter 14 along an axis parallel with the guidewire longitudinal axis without imparting rotational or longitudinal motion to the guidewire 13. The guidewire 13 is slidably received in the lumen 92 of a tubular support member 93 attached to the rotating luer ring 90 and a luer fitting 94. A guidewire delivery catheter 14 may be attached to the device 10 at the luer fitting 94, and rotating the luer ring 90 imparts longitudinal motion in the tubular support member 93, the luer fitting 94, and the delivery catheter 14, but not in the guidewire 13 positioned within the delivery catheter 14. FIG. 14 illustrates the action of the rotating luer ring 90 at line 14a—14a, and the maximum distance of adjustment of the delivery catheter position is about 10 millimeters or more.

As illustrated in FIG. 1, the housing 11 of the vibration device 10 is sized and shaped to fit comfortably in the operator's hand. In operation, the button 55 on the housing 11 is pushed to activate the reciprocating member 54. The guidewire 13 is pushed through a stenotic segment of a vessel as seen in FIG. 1. The guidewire 13 may be secured to the device at the collet 56 and reciprocated, and it is free to rotate even though it is secured to the device. This freedom to rotate results in a vibration device with superior guidewire steerability and ease of use. A delivery catheter 14 may be extended and retracted relative to the guidewire 13 while the guidewire is secured to the device 10, and the delivery catheter may have stiffness and distal end curvature configuration that can be varied while the catheter system remains in the patient.

What is claimed is:

1. A guide wire vibration device, comprising:
   (a) a housing having an interior chamber;
   (b) a drive motor secured within the interior chamber of the housing having a rotary output shaft;
   (c) a cam operatively connected to the output shaft of the motor to convert the rotating output of the rotary output shaft to reciprocating motion;
   (d) an elongated reciprocating member having first and second ends and being operatively engaged at the first end with an operative surface of the cam for reciprocating therewith and pivotably connected at the second end;
   (e) a guidewire tube which has proximal and distal ends, a lumen configured to slidably receive a guidewire and which is secured to the reciprocating member between the proximal and distal ends thereof, so that the guidewire tube reciprocates with the reciprocating member along a longitudinal axis of the guidewire tube; and
   (f) a means for securing the guidewire within the guidewire tube, whereby the guidewire reciprocates with the guidewire tube.

2. The guidewire vibration device of claim 1, wherein the first end of the reciprocating member has a channel defined at least in part by a groove therein which receives the cam.

3. The guidewire vibration device of claim 1 wherein the means for attachment of the guidewire tube to the reciprocating member includes an expanded section centered on a point which bisects the longitudinal axis of the guidewire tube.

4. The guidewire vibration device of claim 3 wherein the reciprocating member has a transverse bore extending through it which is configured to mate with the guidewire tube expanded section for connecting the guidewire tube to the reciprocating member, whereby the guidewire tube reciprocates with the reciprocating member along the guidewire tube's longitudinal axis but remains free to rotate around the guidewire tube's longitudinal axis.

5. The guidewire vibration device of claim 1, wherein the guidewire attachment means comprises a releasably collet which is attached to the guidewire tube and mounted on a proximal side of the device.

6. The guidewire vibration device of claim 1, further comprising means to vary the stroke of the reciprocating lever.

7. The device of claim 6 wherein the means to vary the stroke includes:
   (a) a rotating cap threaded onto the housing of the vibration device; and
   (b) a pivot block attached to the rotating cap such that cap rotation about an axis of the cap imparts linear motion to the pivot block parallel to the cap's axis of rotation, and connected to the reciprocating lever such that the fulcrum of the reciprocating lever is shifted by rotation of the cap, whereby rotation of the cap varies the angle at which the reciprocating lever pivots.

8. A guidewire vibration device of claim 1 wherein the guidewire tube has flat sides and means for attachment to the reciprocating member, so that the guidewire tube reciprocates with the reciprocating member along a longitudinal axis of the guidewire tube but remains free to rotate around the guidewire tube's longitudinal axis;
   a first externally threaded cylindrical extension on a proximal side of the device is positioned so that the guidewire enters the device through the first threaded extension;
   a rotating lock ring is threaded onto the first threaded extension and has
   a plurality of arms, having outer sides and inner sides and tops, with the top of the arms being fixed to the rotating lock ring for longitudinal travel with the rotating lock ring and the arms extending diagonally down into the core of the rotating lock ring forming an opening in the rotating lock ring core through which the guidewire tube extends; and
   a boss is fixed to the housing of the device having an inner face adjacent to the arm outer sides, so that when rotation of the rotating lock ring moves the arms longitudinally towards the device the boss inner face contacts the arm outer sides forcing the arms inward, so that when the rotating lock ring bottom is flush against the device the arm inner sides move into proximity with the guidewire tube, thereby preventing rotation of the guidewire tube but not preventing the guidewire tube longitudinal vibration.

9. A guidewire vibration device, comprising:
   (a) a housing having an interior chamber;
   (b) a drive motor secured within the interior chamber of the housing having a rotary output shaft;
   (c) a cam operatively connected to the output shaft of the motor for converting the rotary output of the rotary output shaft to reciprocating motion;
   (d) a reciprocating member having first and second ends with the first end operatively engaged with an operative surface of the cam to facilitate reciprocation therewith;

(e) a guidewire tube secured to the reciprocating member having a lumen configured to slidably receive a guidewire, so the guidewire tube reciprocates with the reciprocating member along a longitudinal axis of the guidewire tube but remains free to rotate around the guidewire tube's longitudinal axis;

(f) a means for securing the guidewire to the guidewire tube, whereby the guidewire reciprocates and rotates with the guidewire tube;

(g) a second externally threaded cylindrical extension on the distal side of the device positioned so that the guidewire emerges from the device through the second externally threaded cylindrical extension;

(h) a rotating luer ring threaded to attach onto the second threaded extension, so that rotating the luer ring moves it towards and away from the guidewire vibrating device along an axis parallel with the guidewire longitudinal axis;

(i) a tubular support member having a lumen, being positioned so that the guidewire emerges from the vibration device through the tubular support member lumen, and being secured to the rotating luer ring for longitudinal movement with the rotating luer ring; and (j) a luer fitting attached to the tubular support member, for releasably connecting a guidewire delivery catheter to the tubular support member, whereby rotation of the rotating luer ring imparts longitudinal movement in the guidewire delivery catheter independent of the guidewire.

* * * * *